United States Patent [19]

Mendes et al.

[11] Patent Number: 5,618,527
[45] Date of Patent: Apr. 8, 1997

[54] CALCIUM POLYCARBOPHIL SPRINKLE

[75] Inventors: Robert W. Mendes, Dedham; Yuppadee Javroongrit, Boston; Aloysius Anaebonam, Burlington; Emmett Clemente, Manchester, all of Mass.

[73] Assignee: Ascent Pediatrics Inc., Billerica, Mass.

[21] Appl. No.: 240,820

[22] Filed: May 11, 1994

Related U.S. Application Data

[63] Continuation of Ser. No. 953,055, Sep. 30, 1992, abandoned.

[51] Int. Cl.⁶ .................. A61K 31/78; C08J 3/12
[52] U.S. Cl. .......... 424/78.01; 424/78.1; 424/499
[58] Field of Search ................ 424/78.1, 78.01, 424/489, 499, 501

[56] References Cited

U.S. PATENT DOCUMENTS

| | | | |
|---|---|---|---|
| 2,909,462 | 10/1959 | Warfield | 167/56 |
| 3,085,936 | 4/1963 | Caldas et al. | 424/78.01 |
| 3,202,577 | 8/1965 | Markus et al. | 424/78.01 |
| 5,084,278 | 1/1992 | Mehta | 424/497 |
| 5,110,605 | 5/1992 | Acharya | 424/487 |
| 5,336,486 | 9/1994 | Acharya | 424/78.01 |

FOREIGN PATENT DOCUMENTS

| | | |
|---|---|---|
| 10273209 | 7/1988 | European Pat. Off. . |
| 20455561 | 11/1991 | European Pat. Off. . |
| 30488139 | 6/1992 | European Pat. Off. . |
| 49212938 | 1/1993 | Germany . |
| 709091 | 5/1954 | United Kingdom ...... 424/78.1 |

*Primary Examiner*—Peter F. Kulkosky
*Attorney, Agent, or Firm*—Hale and Dorr LLP

[57] ABSTRACT

This invention is directed to pharmaceutical compositions of calcium polycarbophil (CPC) sprinkles. The CPC sprinkles contain very fine calcium polycarbophil powder, with smooth particles, and are processed with one or more excipients to produce a flowable, dispersible composition. For pediatric dosing, the CPC sprinkles are premixed with food and when placed in the mouth, its smooth and creamy consistency makes it easy to ingest without leaving a gritty mouthfeel.

4 Claims, No Drawings

CALCIUM POLYCARBOPHIL SPRINKLE

This application is a continuation, of application Ser. No. 07/953,055, filed 30 Sep. 1992, now abandoned.

FIELD OF THE INVENTION

This invention is directed to a palatable oral composition of calcium polycarbophil.

BACKGROUND OF THE INVENTION

Calcium Polycarbophil U.S.P. ("CPC") is the calcium salt of polycarbophil, which is polyacrylic acid cross-linked with divinyl glycol. Pharmaceutical grade CPC is a water insoluble, hydrophilic, swellable polymer capable of absorbing approximately 35 times its weight of water. The polymer is available from different suppliers in different physical grades which are primarily based on particle size and particle characteristics.

Based on its absorbing and swelling characteristics, CPC is used as a fecal regulator, functioning both as a laxative and anti-diarrheal. In the former case, it draws water to the intestine, swells to form bulk, and causes laxation. In the latter case, it absorbs excess water in the intestine to improve the consistency of watery bowel movements and decrease frequency of bowel movements, thus providing control of diarrhea.

Diarrhea is a major cause of death in children around the world, especially in underdeveloped countries. Even in the United States, diarrhea resulting from both unknown causes and from association with infections, food disorders and allergies represents a significant medical problem.

Diarrhea may be of the acute or chronic type. Although acute diarrhea may be caused by enteric infections, such as dysentery, it is likely that most cases of acute diarrhea are due to abuse of cathartics, ingestion of irritant food, or to minor upsets such as nervous indigestion, acute febrile illnesses or simple fatigue. The etiology in any given case is frequently unknown because of the difficulty of clinically distinguishing one type from another. Symptomatic treatment of the condition, therefore, is usually undertaken without diagnosis. Chronic diarrhea may result from ulcerative colitis, regional inflammation of the bowel, neoplasm, and the like. In such cases, symptomatic treatment is also usually necessary since the cause is often not known or is difficult or impossible to eliminate.

It is well known that diarrheal states are widely prevalent. Similarly, the discomfort and the danger often associated with this condition are also common knowledge. The superimposition of these facts on the difficulty for some people, particularly young children, to ingest existing anti-diarrheal agents emphasizes the tremendous need for an easily administered, effective agent for the symptomatic management of this disease.

Products currently used as anti-diarrheals, available either over-the-counter (OTC) or by prescription (Rx), are primarily intended for use in adults and older children. All have documented problems with respect to side effects and adverse reactions. They are generally of two types—those which reduce intestinal motility through drug action, and those which are intended as adsorbents, primarily clays such as attapulgite and kaolin.

Calcium polycarbophil exhibits few known side effects or adverse reactions, and is apparently not absorbed from the gastrointestinal tract. It is listed as a Category I ingredient in the Tentative Final OTC Monograph.

Presently, CPC is commercially available in the form of tablets intended for swallowing or chewing. None of these forms is entirely suitable for use in pediatric applications, especially for children under six years of age. Children find chewable CPC tablets difficult to swallow because, as the tablets are chewed, they form a rubbery mass which becomes lodged in the child's teeth. The CPC tablets are also objectionable to young children because the CPC tablets have a gritty consistency leaving a poor taste and mouthfeel.

The search for a palatable form of CPC, which is suitable for use by children, has been complicated by the fact that CPC, which is insoluble in water, forms a rubbery mass upon absorbing water to its full capacity. When the particle size is reduced to nearly micron-range by conventional means, the tendency to form a rubbery mass is increased and the sharp-edged particles produce a gritty feeling in the mouth. On the other hand, when the particle size is relatively large, the product is not as rubbery, but it produces the gritty feeling in the mouth due to the sharp edges on the particles.

It was, therefore, an objective of the invention to discover methods of processing CPC to provide palatable forms which could be mixed with or sprinkled on food to allow administration to young children, as well as older children and adults.

SUMMARY OF THE INVENTION

The inventors achieved their objective by the present invention which is directed to pharmaceutical compositions of calcium polycarbophil (CPC) sprinkles. The CPC sprinkles contain very fine calcium polycarbophil powder, with smooth particles, and are processed with one or more excipients to produce a flowable, dispersible composition. For pediatric dosing, the CPC sprinkles are premixed with food and, when placed in the mouth, its smooth and creamy consistency makes it easy for children to ingest without leaving a gritty mouthfeel.

According to this invention, the CPC powder is a pulverized, very fine powder with smooth particle edges. The smooth CPC particle powder can be achieved by milling processes that will not produce sharp edges to the milled powder.

The CPC sprinkle pharmaceutical composition can be made by two processes: a wet granulation process and a dry blending process.

The composition when made by the wet granulation process is a combination of very fine calcium polycarbophil, pulverized by the use of a milling process to produce smooth particle edges, and a wet binder incorporated in such a manner as to facilitate coating and partial agglomeration of the CPC particles to form the CPC sprinkles.

When made by the dry blending process, the composition is a combination of very fine calcium polycarbophil, pulverized by the use of a milling process to produce smooth particles, and one or more excipients having a structure that can entrap and hold the CPC particles. Other excipients can also be added to the mixed CPC and entrapping excipient blend to minimize ambient moisture absorption and to improve the flow characteristics of the CPC sprinkle.

The CPC sprinkles may be mixed with recommended foods, such as apricot sauce, banana and tapioca sauce, to facilitate use by small children.

DETAILED DESCRIPTION OF THE INVENTION

This invention is directed to new pharmaceutical compositions of calcium polycarbophil in a palatable oral powder form. This oral powder form is capable of delivering a therapeutic dose of calcium polycarbophil which is readily and rapidly swallowed.

To make the pharmaceutical compositions, the CPC is pulverized in a milling process to produce a powder with sharp particle edges minimized or eliminated. Milling processes which can be used to produce the CPC powder include attritor mills or ball mills. Those of skill in the art will know of other milling processes which can be used. Hard grinding media can be used with the milling processes. Typically, the grinding media will be ceramic balls, but other material can be used as the grinding media, such as steel. The milling operating conditions necessary to achieve the smooth particle edges will depend upon the starting CPC particle size, the size of the mill, the size of the grinding media, and other parameters that will be known and easily determined by one of skill in the art.

The use of the terms "smooth edges" and "no sharp edges" is meant to describe CPC particles which will not have a gritty feel in the mouth when formulated as a composition of this invention. "Very fine" powder is a term known in the pharmaceutical art and is defined as particles that pass through a No. 120 sieve (sieve opening 125 um). There is no limit as to greater fineness of powder size that can be used in this invention. It will be recognized by one of skill in the art that the objective is to reduce or eliminate sharp edges of the CPC particles and that the exact particle size is not critical. A simple measure of whether the CPC particles have smooth edges or sharp edges can be done by a mouthfeel test to determine whether the CPC particles have a gritty consistency.

Wet Granulation Process

CPC sprinkles of this invention can be prepared by coating the very fine calcium polycarbophil powder with a binder in a wet granulation process. A granulation process results in a coated and partially agglomerated calcium polycarbophil powder.

The binder of the composition may be any natural or synthetic compound, or combination of compounds, which provides adequate binding to produce partial agglomeration and coating of the drug. The preferred binder is also a sweetener to overcome the blandness of the CPC. Binders that are also natural sweeteners include carbohydrates such as sucrose, dextrose, fructose, invert sugar, mannitol, and sorbitol. As mentioned, a binder can be combined with one or more sweetener. Synthetic sweeteners that can be used include saccharin, aspartame, and cyclamates. Those skilled in the art will know, or will be able to ascertain with no more than routine investigation, other natural or synthetic sweeteners that may be used to prepare the composition of this invention. Electrolytes may also be added as supplements to treat electrolyte loss. Electrolytes that may be part of the CPC sprinkle include sodium and potassium chlorides and the like.

The ratio of binder solids to calcium polycarbophil powder is preferably between about 50:50 to about 5:95, and more preferably 20:80.

The wet granulation systems that can be used according to this invention include the following: consolidation granulation, such as by planetary or Horbart equipment, and fluidized bed drying; consolidation blending and air or tray drying; and fluidized bed granulation and drying.

The following description describes planetary granulation and tray drying by way of example only. Those of skill in the art will be able to ascertain the optimum conditions for other wet granulation systems to produce the CPC sprinkles of this invention.

Typically, the very fine calcium polycarbophil powder is placed in an agglomerating vessel. The binder solution is sprayed or slowly added to the powder at a specified rate, forming a partially agglomerated mass of powder. The mixing of the calcium polycarbophil and the binder is continued, depending upon the equipment used and the size of the batch. The mixing should continue for a length of time to ensure adequate distribution of the binder, and if preferred, also the sweetener, throughout the mass of the calcium polycarbophil. Without the coating and agglomerating, calcium polycarbophil is difficult to handle due to its fluffy nature and its tendency to rapidly hydrate and clump when wetted.

The thus formed agglomerated mass of powder is removed from the vessel. At this point the granules are screened to form more uniform granules. The screened granules are dried, typically by air drying or with mild heat, on trays and may be occasionally moved about on the drying trays to prevent adhesion of the granules. The calcium polycarbophil sprinkle is typically dried at a temperature of between about 20° C. to about 50° C. for a period of up to about 48 hours. The dried granules are then screened to the desired size, using a screen or a mill having a mesh size preferably of between about screen No. 8 (sieve opening 2.36 mm) and screen No. 20 (sieve opening 850 um). A second drying of the thus screened final product can also be performed to remove any excess moisture.

Dry Blending

Another method of producing the CPC sprinkles of this invention is by dry blending the very fine calcium polycarbophil with one or more excipients that has a structure which is capable of entrapping and holding the very fine CPC powder to form a stable dispersion without the use of a binder. The exact structure of the excipient is not critical provided that the CPC particles can be trapped so that the blended pharmaceutical composition will be able to flow and disperse. The use of the term "excipient" is well known in the pharmaceutical arts and is defined as a non-active ingredient which does not affect the activity of the active ingredient or drug. The excipients that can be used in this invention are monosaccharides, disaccharides and polysaccharides or their polymers that are capable of forming a mesh-like, honeycomb or "pollen-like" structure, for example, when subjected to conventional or specialized spray-drying. In addition to entrapping the CPC powder, the preferred excipients also impart good flow properties to the sprinkles and act as moisture scavengers, thereby ensuring stability of the product. The excipients also improve the dispersibility of the calcium polycarbophil in select aqueous-based foods without localized gelling or massing of the CPC.

The preferred excipient to entrap the CPC particles is Sorbitol Instant®, a spray-dried form of sorbitol, available from EM Industries Inc. The spray-dried sorbitol component with its mesh-like structure entraps the very fine calcium polycarbophil, forming a stable dispersion without the use of a binder. The amount of the spray-dried sorbitol ranges from 0.5 to 5 times the weight of calcium polycarbophil. The spray-dried sorbitol also improves the flow properties of the entrapped calcium polycarbophil as a result of its near spherical shape and shields the susceptible calcium polycarbophil from the undesirable effects of ambient moisture. Sorbitol also imparts a slightly sweet taste to the CPC sprinkles.

In the preferred CPC sprinkle composition, the excipient and trapped CPC blend can be mixed with one or more other excipients. The other excipients are selected to improve the flow characteristics, to act as a dispersant of the sprinkles in food, and to reduce the absorption of ambient moisture. These bulking and function modifying excipients can include spray dried or specialty processed monosaccharides, disaccharides and polysaccharides; glucose polymers derived from starch and various blends of the above excipients.

Two of the preferred excipients include Maltodextrin M550®, a specialty processed spray-dried, water soluble glucose polymers derived from starch, available from Grain Processing Co., Muscatine, Iowa and Cantab®, a specialty processed dextrose, available from Penford Products Company, Cedar Rapids, Iowa.

Maltodextrin M550® has excellent flow characteristics and low bulk density and functions in the formulation as an inert carrier/bulking agent that also improves the flow properties of the product. The Maltodextrin M550® due to its very good water solubility also acts as a dispersant of the sprinkles when the sprinkles are added to semi-solid foods. This leads to the formation of a smooth dispersion of the sprinkles in the food without localized gelling or massing. The Maltodextrin M550®, as a result of its particle characteristics and product properties, also functions as a moisture scavenger, thus protecting the sprinkles from the adverse effects of ambient moisture, and thus ensuring an excellent solid state stability for the sprinkles.

The other component of the preferred composition, Cantab®, in addition to improving the flow properties of the product, also functions as a bulking agent. Cantab®, due to its very high rate of solution, provides instant dispersion of the sprinkles in recommended foods. When the product is taken alone, the Cantab® provides a smooth texture to the sprinkles and produces a cool mouthfeel due to negative heat of solution.

The sprinkles formed by the dry blending process may also contain sweeteners or electrolytes as supplements in the treatment of diarrhea accompanied by electrolyte loss. Natural sweeteners that may be incorporated include carbohydrates such as sucrose, dextrose, fructrose, invert sugar, mannitol and the like. Synthetic sweeteners include saccharin, aspartame, cyclamates and other so-called "artificial sweeteners" familiar to those of skill in the art. Electrolytes that may be part of the CPC sprinkle include sodium and potassium chlorides and the like.

The method of producing the dry blended CPC sprinkles will be described using the preferred embodiment by way of example only.

The blended composition is formed by first entrapping the very fine calcium polycarbophil in the mesh-like structure of the Sorbitol Instant®. This is accomplished by placing the very fine calcium polycarbophil and the Sorbitol Instant® in a suitable blender, such as a tumbling mixer blender and mixing the two materials at a slow speed until a good pre-mix is achieved, typically from about 15 minutes up to 60 minutes. This results in a pre-mix of uniformly entrapped calcium polycarbophil in Sorbitol Instant®. The other two excipients, Maltodextrin M550® and Cantab®, are then added and the mixing continued until a uniform blend is achieved, typically for an additional 10 minutes to 25 minutes.

The ratio of Sorbitol Instant® to CPC may be between 0.5:1 to 5:1 parts relative to each other. The other excipients (Maltodextrin M550® or Cantab®) may constitute from 0% up to 50% of the formulation.

The calcium polycarbophil sprinkle of this invention can be used to treat a patient afflicted with diarrhea. A therapeutically effective amount of the pharmaceutical composition is orally administered to the patient. Preferably, the composition is mixed with, or sprinkled on, the patient's food. This is a particularly advantageous method of administering this anti-diarrheal agent to children and the elderly who may have difficulty swallowing medications. When the pharmaceutical composition is premixed with food and placed in the mouth, its smooth and creamy consistency makes it easy to ingest without leaving a gritty mouthfeel. Further, the pharmaceutical composition, which is mildly sweetened, will not adversely affect the taste of the food.

A therapeutically effective amount of the pharmaceutical composition of this invention is that quantity which will alleviate the symptoms of a patient suffering from diarrhea. The preferred therapeutically effective quantity for adults (twelve years and older) is an oral daily dosage of 1 gram four times a day or 2 grams three times a day or as needed, not to exceed 6 grams in 24 hours. The preferred dosage for children (six to under twelve years) is an oral daily dosage of 0.5 to 1 gram three times a day or as needed, not to exceed 3 grams in 24 hours. The preferred dosage for children (three to under six years) is an oral daily dosage of 0.33 to 0.5 grams three times a day or as needed, not to exceed 1.5 grams in 24 hours.

For these dosages, a preferred ratio of the entrapment excipient (Sorbitol Instant®) to CPC may be 1:1 parts relative to each other for a ½ gram product and 2:1 parts for a ⅙ gram product. The preferred combined level of the bulking and function modifying excipients is 22.5% for a ½ gram product and 25% for a ⅙ gram product.

The actual quantity given in a specific case will vary according to the clinical needs of the patient. Those skilled in the art will know, or will be able to ascertain with no more than routine experimentation, the precise dosage required in any given situation.

The invention is illustrated further by the following examples, which are not to be taken as limiting in any way.

EXAMPLES

Example 1—Wet Granulation

A wet granulation formula and processing directions utilizing the Hobart® (planetary) mixer was used in this example.

Formulation

| | |
|---|---|
| Calcium polycarbophil, very fine | 100 g |
| 70% sorbitol solution | 20–30 mL |
| Purified Water | as needed |

Procedure

1. The calcium polycarbophil very fine powder was placed in the bowl of the Hobart® planetary mixer.

2. The sorbitol solution was slowly added while operating the mixer on speed #1, over a period of about 5 minutes.

3. Additional water was added as needed with continued mixing to assure an appropriate wet granulation end-point.

4. The dampened mass was removed from the mixer bowl, spread on stainless steel trays at a shallow depth, and allowed to partially air-dry for about 24 hours.

5. The granules were screened with a No. 20 mesh stainless steel screen.

6. The screened granules were returned to the trays and dried at 49° C. for about 22 hours.

7. The calcium polycarbophil sprinkle was collected into suitable containers.

Example 2—Dry Blending

Formulation A

| Ingredient | 100.0 g |
| --- | --- |
| Calcium polycarbophil | 37.5 |
| Sorbitol Instant ® Pharma NF, FCC | 40 |
| Maltodextrin M550 ® | 12.5 |
| Cantab ® | 10 |

Formulation B

| Ingredient | 100.0 g |
| --- | --- |
| Calcium polycarbophil | 25 |
| Sorbitol Instant ® Pharma NF, FCC | 50 |
| Maltodextrin M550 ® | 15 |
| Cantab ® | 10 |

Procedure

1. The calcium polycarbophil was placed in the V-shaped Patterson-Kelly Twin-shell blender.

2 The sorbitol was added and pre-mixed for 10 minutes at low speed.

3 The Maltodextrin M550® and Cantab® were added to the contents of the blender and the blending continued at low speed for an additional 10 minutes. (Total blending time=20 minutes.)

4. The material was collected into suitable containers.

Example 3—CPC Sprinkles

Physical Properties

Taste test—A sample of the composition was subjected to taste testing by a group of trained scientists and was most often described as a "melt in your mouth" product.

Taste and mouthfeel after mixing with food—When mixed with food, the product dispersed very uniformly and had a very good mouthfeel.

Although the foregoing invention has been described in some detail by way of illustration and example for purposes of clarity of understanding, it will be obvious to one skilled in the art that certain changes and modifications may be practiced within the scope of the appended claims.

What is claimed is:

1. An oral pharmaceutical composition, consisting essentially of a flowable, dispersible composition formed by wet-blending together (1) very fine calcium polycarbophil powder particles produced by milling calcium polycarbophil using an attritor mill such that the resultant very fine calcium polycarbophil powder particles have smooth edges with a good mouthfeel, with (2) a binder component comprising one or members selected from the group consisting of sucrose, dextrose, fructose, invert sugar, mannitol, sorbitol, saccharin, aspartame, and cyclamates and optionally with (3) an electrolyte component comprising one or members of selected from a group consisting of sodium chloride and potassium chloride, wherein the ratio of said very fine calcium polycarbophil powder particles to said binder is about 80 to about 20 and said very fine calcium polycarbophil powder particles (1) and said binder component (2) are blended for a length of time effective to granulate and coat said very fine powder particles with binder.

2. An oral pharmaceutical composition, consisting essentially of a flowable, dispersible composition formed by dry-blending together (1) very fine calcium polycarbophil powder particles produced by milling calcium polycarbophil using an attritor mill to produce very fine calcium polycarbophil powder particles having smooth edges with a good mouthfeel; with (2) an entrapping excipient comprising one or more members selected from the group consisting of a monosaccharide, disaccharide, polysaccharide, a polymer of monosaccharide, a polymer of a disaccharide, and a polymer of a polysaccharide, said entrapping excipient forming a mesh-like structure such that said very fine calcium polycarbophil powder particles are entrapped within said mesh-like structure; and then dry-blending the resultant blending (1) and (2), with (3) a bulking and function modifying excipient comprising one or more members selected from the group consisting of a monosaccharide, a disaccharide, a polysaccharide, and a glucose polymer derived from starch, and optionally with (4) a sweetener component comprising one or more sweeteners selected from the group consisting of sucrose, dextrose, fructose, invert sugar, mannitol, saccharin, aspartame, and cyclamates, and optionally with (5) an electrolyte component comprising one or members selected from a group consisting of sodium chloride and potassium chloride.

3. The oral pharmaceutical composition of claim 2, wherein said entrapping excipient is Sorbitol Instant®, and said bulking and function modifying excipient comprises Maltodextrin M550® and Cantab®.

4. The oral pharmaceutical composition of claim 3, wherein said sorbitol instant is present in an amount of from 0.5 to 5 times the weight of said very fine calcium polycarbophil powder particles.

* * * * *